US00PP25513P2

(12) United States Plant Patent
Hanna et al.

(10) Patent No.: US PP25,513 P2
(45) Date of Patent: May 5, 2015

(54) GRASS 'TIFT 26'

(50) Latin Name: ***Pennisetum* hybrid**
Varietal Denomination: Tift 26

(71) Applicant: University of Georgia Research Foundation, Inc., Athens, GA (US)

(72) Inventors: Wayne W. Hanna, Chula, GA (US); S. Kristine Braman, Griffin, GA (US); Brian M. Schwartz, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 153 days.

(21) Appl. No.: 13/986,883

(22) Filed: Jun. 13, 2013

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Klarquist Sparkman, LLP

(57) ABSTRACT

The new variety *Pennisetum* 'Tift 26' is provided. The new and distinct variety has high ornamental value, cold tolerance for short periods of time, and disease resistance. The asexually reproduced variety is reliably propagated vegetatively.

1 Drawing Sheet

Latin name of the genus and species of the plant claimed: 'Tift 26' is a tri-specific ornamental *Pennisetum* hybrid of the genus and species *Pennisetum purpureum*×[*Pennisetum glaucum*×(*Pennisetum purpureum*×*Pennisetum squamulatum*)].

Variety denomination: The new *Pennisetum* claimed is of the variety denominated 'Tift 26'.

BACKGROUND OF THE INVENTION

The present invention relates to a new and distinct cultivar of *Pennisetum* herein referred to as 'Tift 26'.

The new *Pennisetum* 'Tift 26' is a product of a planned breeding program conducted by the Inventors in Tifton, Ga. The objective of the *Pennisetum* breeding program is to create new plant cultivars with improved commercial qualities. This cultivar is commercially important for its superior ornamental value. These and other qualities are enumerated herein.

Pedigree and history: In 2003, red tetraploid (2n=4x=28) pearl millet (unpatented *Pennisetum glaucum*; designated '04-94') was crossed with SC 1125-2 [a Merkeron napiergrass (unpatented *Pennisetum purpureum;* 2n=4x=28) that had been crossed with PS 262 (unpatented *Pennisetum squamulatum;* 2n=8x=56)]. One vigorous plant, from the 04-94/SC 1125-2 cross, designated '04-26-1,' was selected in 2004. In 2004, 'Princess' napiergrass (U.S. Plant Pat. No. 17,728; 2n=4x=28, female parent) was pollinated with '04-26-1' (unpatented; male parent). The new variety 'Tift 26' was the twenty-sixth plant selected in 2005 from the 2004 cross. The new variety 'Tift 26' has been tested since 2007.

Asexual reproduction of the new *Pennisetum* 'Tift 26' by vegetative propagation (single stem propagules) in a controlled environment in Tifton, Blairsville, and Griffin, Ga. since 2007, has shown that the unique features of this new *Pennisetum* hybrid are stable and reproduced true to type in successive generations.

SUMMARY OF THE INVENTION

The following traits have been repeatedly observed and represent the characteristics of a new variety *Pennisetum*, 'Tift 26'. The new variety 'Tift 26' has not been observed under all possible environmental conditions. The phenotype may vary somewhat with variations in, for example, temperature, day-length, light intensity, soil types, and water and fertility levels without, however, any variance in genotype.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following traits have been repeatedly observed in Tifton, Blairsville, and Griffin, Ga., and are determined to be the unique characteristics of the new variety 'Tift 26':

1. 'Tift 26' reaches a height of about 1.4 meters, and a spread of about 1.4 meters.
2. 'Tift 26' exhibits a vigorous growth habit.
3. 'Tift 26' is pollen and seed sterile.

The new variety *Pennisetum* 'Tift 26' can be compared to its parents, 'Princess' and '04-26-01,' and 'Tift 10,' described in a soon to be pending U.S. Plant Patent Application.

Plants of the new *Pennisetum* 'Tift 26' differ from its female parent 'Princess' in the following characteristics:

1. The new variety 'Tift 26' is taller than 'Princess'.
2. 'Tift 26' has wider and longer leaves than 'Princess'.
3. 'Tift 26 does not have the mottled grey-purple/green color of 'Princess'.

Plants of the new *Pennisetum* differ from its male parent '04-26-1' in the following characteristics:

1. The new variety 'Tift 26' is slightly different from '04-26-1' in adaxial leaf color. The new variety 'Tift 26' is about Greyed-purple RHS 187C, whereas '04-26-1' is about mottled Greyed-purple/green RHS 183B/138A.
2. The new variety 'Tift 26' has a different midrib color. The new variety 'Tift 26' is about Greyed-purple RHS 186B, while '04-26-1' is about Red-purple RHS 61C.

Plants of the new *Pennisetum* 'Tift 26' differ from its sister hybrid 'Tift 10' in the following characteristics:

1. The new variety 'Tift 26' is significantly shorter than 'Tift 10'.

The following observations, measurements, and values describe plants grown in Tifton, Blairsville, or Griffin, Ga. In Tables 1-5, the least significant difference (LSD) is set at P≤0.05 probability level. Growth days were included in ratings. Plants were spaced at 2 meter centers. All data are from plants established as single stem propagules in mid-May and rated in September through October, except the data from 2010 and 2011, in which the plants had been overwintered at Tifton, Ga.

The new variety 'Tift 26' was significantly shorter than 'Tift 10' in four tests (all tests in Tifton, Ga. and one test in Blairsville, Ga.), but was not significantly different in height in four tests (two tests in Blairsville, Ga. and all tests in Griffin, Ga.) (Table 1). The canopy diameter for 'Tift 26' was equal to that of 'Tift 10' in five of eight tests and significantly wider in three of eight tests (Table 2). 'Tift 26' has an attractive reddish/purple color and was equal to 'Tift 10' in two tests, significantly better in one test, and significantly less (with 'Tift 26' still maintaining an attractive color) in five tests (Table 3). The new variety 'Tift 26,' similar to 'Tift 10,' is not disease-susceptible to *Helminthosporium* leaf spot, whereas 'Princess' is susceptible to this disease (Table 4). Leaves of 'Tift 26' are significantly narrower, but similar in length, and leaf area compared to the leaves of 'Tift 10' (Table 5). There was no significant difference in culm-leaf angle between 'Tift 26' and 'Tift 10' (Table 5).

TABLE 1

Plant heights (cm) of two ornamental *Pennisetum* grasses planted at three locations in Georgia.

| | Tifton | | | Blairsville | | | Griffin | |
|---|---|---|---|---|---|---|---|---|
| | 2009 | 2010 | 2011 | 2009 | 2010 | 2011 | 2009 | 2010 |
| Growth days | 153 d | 150 d | 183 d | 144 d | 145 d | 160 d | 138 d | 124 d |
| 'Tift 26' | 98 | 97 | 85 | 137 | 128 | 120 | 151 | 124 |
| 'Tift 10' | 117 | 125 | 103 | 156 | 129 | 138 | 153 | 136 |
| LSD | 7 | 15 | 14 | 24 | NS | NS | NS | NS |

In Table 1, plant heights were measured from ground level to top of plant canopy. All height measurements are in cm. At Tifton, Ga., 'Tift 26' and 'Tift 10' were planted on May 9, 2009, May 9, 2010, and May 12, 2011, with measurements taken on Oct. 12, 2009, Sep. 29, 2010, and Oct. 18, 2011. At Blairsville, Ga., 'Tift 26' and 'Tift 10' were planted on May 14, 2009, May 11, 2010, and May 1, 2011, with measurements made on Oct. 8, 2009, Oct. 6, 2010 and Oct. 10, 2011, respectively. At Griffin, Ga., 'Tift 26' and 'Tift 10' were planted on May 14, 2009 and May 14, 2010, with measurements taken on Oct. 2, 2009 and Sep. 10, 2010.

TABLE 2

Canopy diameter (cm) of individual plant of two ornamental *Pennisetum* grasses planted at three locations in Georgia. Plants were spaced on two meter centers.

| | Tifton | | | Blairsville | | | Griffin | |
|---|---|---|---|---|---|---|---|---|
| | 2009 | 2010 | 2011 | 2009 | 2010 | 2011 | 2009 | 2010 |
| Growth days | 153 d | 150 d | 183 d | 144 d | 145 d | 160 d | 138 d | 124 d |
| 'Tift 26' | 177 | 124 | 122 | 159 | 157 | 145 | 153 | 156 |
| 'Tift 10' | 139 | 130 | 109 | 156 | 147 | 140 | 144 | 156 |
| LSD | 7 | NS | 10 | NS | 15 | NS | NS | NS |

Plant canopy measurements, as shown in Table 2, represent the average diameters measured at the estimated widest and narrowest portions of a single plant canopy. Measurements are in cm. At Tifton, Ga., 'Tift 26' and 'Tift 10' were planted on May 9, 2009, May 9, 2010, and May 12, 2011, with measurements taken on Oct. 12, 2009, Sep. 29, 2010, and Oct. 18, 2011. At Blairsville, Ga., 'Tift 26' and 'Tift 10' were planted on May 14, 2009, May 11, 2010 and May 1, 2011, with measurements made on Oct. 8, 2009, Oct. 6, 2010 and Oct. 10, 2011. At Griffin, Ga., 'Tift 26' and 'Tift 10' were planted on May 14, 2009 and May 14, 2010, with measurements taken on Oct. 2, 2009 and Sep. 10, 2010.

TABLE 3

Color ratings on individual plants of two ornamental *Pennisetum* grasses planted at three locations in Georgia. Plants were spaced on two meter centers.

| | Tifton | | | Blairsville | | | Griffin | |
|---|---|---|---|---|---|---|---|---|
| | 2009 | 2010 | 2011 | 2009 | 2010 | 2011 | 2009 | 2010 |
| Growth days | 153 d | 150 d | 183 d | 144 d | 145 d | 160 d | 138 d | 124 d |
| 'Tift 26' | 8.6 | 7.8 | 8.1 | 8.0 | 8.0 | 8.6 | 7.6 | 8.0 |
| 'Tift 10' | 9.0 | 9.0 | 7.6 | 9.0 | 8.0 | 9.0 | 9.0 | 7.6 |
| LSD | 0.2 | 0.9 | 0.4 | 0.7 | NS | 0.6 | 0.7 | NS |

Color ratings are measured on a scale of 1 to 9, where 1 represents green and 9 represents dark purple/red. At Tifton, Ga., 'Tift 26' and 'Tift 10' were planted May 9, 2009, May 9, 2010, and May 12, 2011, with measurements taken on Oct. 12, 2009, Sep. 29, 2010, and Oct. 18, 2011. At Blairsville, Ga., 'Tift 26' and 'Tift 10' were planted on May 14, 2009, May 11, 2010 and May 1, 2011, with measurements taken on Oct. 8, 2009, Oct. 6, 2010 and Oct. 10, 2011. At Griffin, Ga., 'Tift 26' and 'Tift 10' were planted on May 14, 2009 and May 14, 2010, with measurements taken Oct. 2, 2009 and Sep. 10, 2010.

TABLE 4

*Helminthosporium* leaf spot ratings on two ornamental *Pennisetum* grasses planted at three locations in Georgia.

| | Tifton | | | Blairsville | | Griffin |
|---|---|---|---|---|---|---|
| | 2009 | 2010 | 2011 | 2010 | 2011 | 2009 |
| Growth days | 153 d | 150 d | 183 d | 145 d | 160 d | 138 d |
| 'Tift 26' | 1.0 | 1.0 | 1.0 | 1.0 | 1.0 | 1.0 |
| 'Tift 10' | 1.0 | 1.0 | 1.0 | 1.0 | 1.0 | 1.0 |
| 'Princess' | 5.2 | 6.6 | 8.0 | 5.0 | 7.6 | 6.6 |
| LSD | 0.4 | 0.1 | 0.0 | 1.2 | 0.2 | 0.6 |

Disease ratings in Table 9 are defined as follows: 1=No disease, 2=1-20%, 3=21-30%, 4=31-40%, 5=41-50%, 6=51-60%, 7=61-70%, 8=71-80%, 9=>80% leaves infected. Symptoms occur in the field during late August and September. At Tifton, Ga., 'Tift 26' and 'Tift 10' were planted on May 9, 2009, May 9, 2010, and May 12, 2011, with measurements taken on Oct. 12, 2009, Sep. 29, 2010, and Oct. 18, 2011. At Blairsville, Ga., 'Tift 26' and 'Tift 10' were planted on May 11, 2010 and May 1, 2011, with measurements taken on Oct. 6, 2010 and Oct. 10, 2011. At Griffin, Ga., 'Tift 26' and 'Tift 10' were planted on May 14, 2009, with measurements taken on Oct. 2, 2009.

TABLE 5

Leaf characteristics of individual plants of two ornamental *Pennisetum* grasses planted at Tifton, Georgia in 2009. Plants were spaced on two meter centers.

| Entry | Leaf Length(cm) | Leaf Width(mm) | Leaf Area($cm^2$) | Leaf Angle Culm:Leaf |
|---|---|---|---|---|
| 'Tift 26' | 72 | 40 | 206 | 13 |
| 'Tift 10' | 74 | 45 | 230 | 15 |
| LSD | NS | 4 | NS | NS |

The leaf length was measured in cm from the leaf collar to the leaf tip of the latest fully extended leaf. The leaf width was measured in mm in the center of the latest fully extended leaf. The leaf area was measured in $cm^2$ using a LiCor area meter using the mean of three leaves per replication. The measured leaf angle was the angle observed between the adaxial leaf angle surface and the culm at the leaf collar on the last fully extended leaf and was measured in degrees. At Tifton, Ga., 'Tift 26' was planted on May 9, 2009, with measurements taken on Sep. 12, 2009.

TABLE 6

Summary of morphological characteristics of two *Pennisetum* grasses.

| Trait | 'Tift 10' | 'Tift 26' |
|---|---|---|
| Mature plant height | 103-156 cm | 85-151 cm |
| Diameter of plant canopy | 109-156 cm | 122-157 cm |
| Leaf width | 45 mm | 40 mm |
| Leaf length | 74 cm | 72 cm |
| Leaf Area-$cm^2$ | 230 | 206 |
| Leaf Angle (Stem:Leaf) | 15 degrees | 13 degrees |
| Adaxial leaf surface trichomes | Sparse, 1.0 mm | Moderate, less than 1 mm along either side of midrib |
| Abaxial leaf surface trichomes | None | None |
| Leaf blade margin trichome length | Continuous, less than 1.0 mm | 0.5 mm |
| Leaf collar trichome length | Dense, 4 mm | Dense, 3 mm |
| Leaf blade edge at collar Trichome | 5 mm long for 7 cm from collar | 5 mm long for 4 cm from collar |
| Sheath trichomes | None | Dense, 1 mm |
| Adaxial leaf color | Greyed-purple 187A | Greyed-purple 187C |
| Abaxial leaf color | Greyed-purple 186A | Greyed-purple 186B |
| Midrib color | Greyed-purple 186B | Greyed-purple 186B |
| Inflorescences on Dec. 21, 2009 | Yes | Yes |
| *Helminthosporium* leaf spot on mature plants | None | None |

In summary, 'Tift 26' is similar to 'Tift 10' in canopy diameter, disease resistance, leaf length, and culm-leaf angle. 'Tift 26' tends to be taller, to have narrower leaves, and to not have as dark reddish/purple color leaves as 'Tift 10'.

BRIEF DESCRIPTION OF THE FIGURES

The accompanying colored photographs illustrate the overall appearance and distinct characteristics of the new variety of *Pennisetum* 'Tift 26'. The colors in the photographs are as close as possible with the photographic and printing technology utilized.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

FIG. 1 is a photograph of the new variety *Pennisetum* 'Tift 26'.

BOTANICAL DESCRIPTION

The new variety 'Tift 26' is a perennial at Tifton, Ga. (USDA Zone 8a). The new variety 'Tift 26' survived −7° C. for one night and 24 nights below 0° C. in the field during the 2010/2011 winter at Tifton. It has survived the winter temperatures (60 nights below 0° C. and a low temperature of −8° C. in the field during 2009/2010) in Griffin, Ga. (USDA Zone 7b). It has not survived the winter temperatures (lows of −15° C. in 2009/2010 and 2010/2011) in the mountains of Blairsville, Ga. (USDA Zone 6b). Because of its vigor, 'Tift 26' can effectively be used as an annual where it will not survive freezing temperatures in the winter.

All data are from plants established as single stem propagules in mid-May, and rated in September through October, except the 2010 and 2011 data are from plants that over-wintered at Tifton. Plants were spaced at 2 meter centers.

Plant:

*Mature plant height*.—Approximately 85-151 cm.

*Diameter of plant canopy*.—Approximately 122-157 cm.

Leaf:

*Leaf width*.—Approximately 40 mm.

*Leaf length*.—Approximately 72 mm.

*Adaxial leaf surface trichomes*.—Moderate, less than 1 mm along either side of midrib.

*Abaxial leaf surface trichomes*.—None.

*Leaf blade margin trichome length*.—0.5 mm.

*Leaf collar trichome length*.—Dense, 3 mm.

*Leaf blade edge at collar trichome*.—5 mm long for 4 cm from collar.

*Sheath trichomes*.—Dense, 1 mm.

*Adaxial leaf color*.—About Greyed-purple RHS 187C.

*Abaxial leaf color*.—About Greyed-purple RHS 186B.

*Midrib color*.—About Greyed-purple RHS 186B.

*Helminthosporium leaf spot on mature plants*.—None.

*Inflorescence on Dec.* 21, 2009.—Yes.

What is claimed is:

1. A new and distinct variety of the *Pennisetum* plant named 'Tift 26,' substantially as illustrated and described herein.

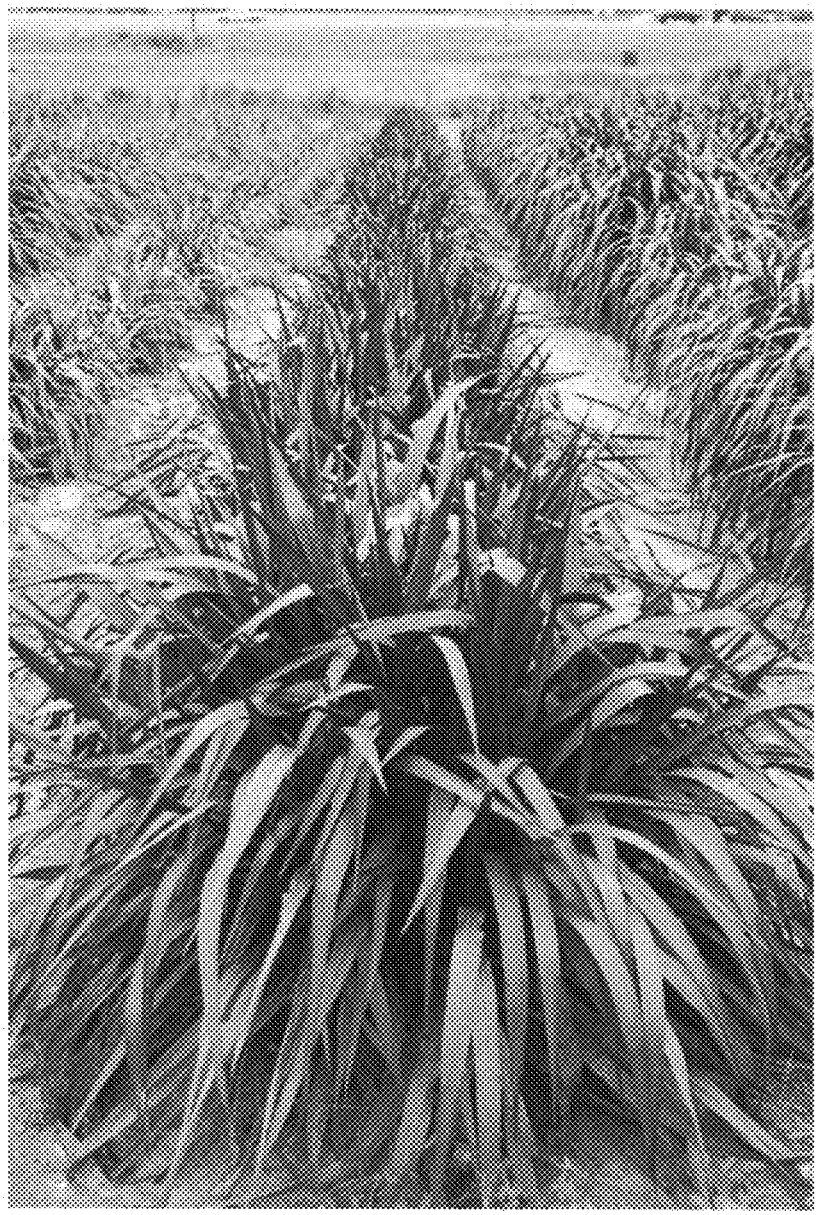

* * * * *